(12) United States Patent
Minden

(10) Patent No.: US 6,342,143 B1
(45) Date of Patent: Jan. 29, 2002

(54) CUTTING TOOL FOR MULTIPLE SAMPLE RETRIEVAL FROM GELATINOUS MATERIAL

(75) Inventor: Jonathan S. Minden, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 09/478,664

(22) Filed: Jan. 6, 2000

(51) Int. Cl.[7] .............................................. G02N 27/26
(52) U.S. Cl. ........................ 204/462; 204/466; 204/613; 204/616; 435/287.1
(58) Field of Search ................................ 204/450, 457, 204/462, 466, 600, 606, 616, 613; 435/287.1, 287.2, 287.3, 288.7, 288.6

(56) References Cited

U.S. PATENT DOCUMENTS

| 4,938,593 | A | * | 7/1990 | Morris et al. ................ | 356/344 |
| 5,217,591 | A | | 6/1993 | Gombocz et al. ........... | 204/466 |
| 5,587,062 | A | | 12/1996 | Togawa et al. ............. | 204/613 |
| 5,638,170 | A | | 6/1997 | Trinka et al. ................ | 356/244 |

FOREIGN PATENT DOCUMENTS

| JP | 361061039 A | * | 3/1986 |
| WO | WO 98/23950 | | 6/1998 |
| WO | WO 99/15875 | | 4/1999 |

OTHER PUBLICATIONS

JPAB abstract of Okubo et al. (JP 361061039 A).*

* cited by examiner

Primary Examiner—Jill Warden
Assistant Examiner—Alex Noguerola
(74) Attorney, Agent, or Firm—Kirkpatrick & Lockhart LLP

(57) ABSTRACT

The invention relates to a sample retrieval apparatus of particular benefit in the field of molecular biology. The apparatus permits the rapid collection of numerous specified fractions of samples: such as DNA, RNA or protein, that are separated by gel electrophoresis; or microorganisms grown on agar plates. The apparatus is capable of multiple sample retrieval from gels without cross-sample contamination from previously excised samples. Specifically, the sample retrieval apparatus is able to engage a cutting tip, cut a desired spot, band or plaque from a gel, deposit the desired band or plaque into a container, such as a multi-well plate for processing, and disengage the used cutting tip. The apparatus is then able to repeat this process many times to facilitate rapid and accurate processing of multiple bands or plaques from a single gel using different cutting tips for each sample retrieval.

26 Claims, 6 Drawing Sheets

CUTTING TOOL FOR MULTIPLE SAMPLE RETRIEVAL FROM GELATINOUS MATERIAL

FEDERALLY SPONSORED RESEARCH

This research is partially sponsored by: the National Institutes of Health, grant number R01-HG01724; and the Human Genome Institute. The United States Government may have rights in this invention.

CROSS-REFERENCE TO RELATED APPLICATIONS

Not Applicable.

BACKGROUND OF THE INVENTION

In the field of molecular biology, many tools have been developed for analyzing biomolecules. One such tool, electrophoresis, enables one to separate biomolecules, such as DNA, RNA and protein, based upon size, shape and/or charge. A mixture of biomolecules are placed in small wells in a gel, typically, a polyacrylamide gel, and a charge is applied which separates the biomolecules into discrete bands. The ability to separate biomolecules allows for the isolation and purification of many different biomolecule samples or bands in a single gel. Once isolated, a single band can be analyzed to determine a purified biomolecule's unique properties. In addition, isolation of purified biomolecules facilitates diagnosis of certain diseases and other biological abnormalities.

Isolation of the samples has had some shortcomings. One of these shortcomings is cross-sample contamination, which can occur when the same scalpel or razor blade is used to excise different biomolecules from the gel. To isolate samples, the area of the gel containing the desired band is cut with a scalpel or razor blade. Conventional gel cutting tools, such as the tool described in U. S. Pat. No. 5,587,062, do not provide for replacement of the cutting tool for each gel sample excised. Therefore, only one contamination-free sample can be excised. Subsequent samples can not be excised using the same cutting tool without contamination.

Agarose gels are used to grow bacteria and other microorganisms. An agarose plate is streaked, for example, with a sample to be tested. Microorganisms typically grow in plaques on the gel. The plaques can be excised from the gel. The contamination problems that exist with electrophoresis gels are also experienced with agarose gels.

As a result, there is a need for a gel cutting apparatus capable of multiple sample retrieval without cross-contamination from previously excised samples.

BRIEF SUMMARY OF THE INVENTION

The present invention provides a sample retrieval apparatus that includes a support platform, a support translation member for moving the support platform to designated coordinates on X and Y axes, a cutter member, a cutter translation assembly for moving the cutter member to designated positions on a Z axis, the Z axis lying in a plane perpendicular to the support platform, and, a controller for designating the X, Y axis coordinates of the support platform and the Z axis positions of the cutter member. The support translation member has an elongate X rail lying on the X axis and an elongate Y rail lying on the Y axis. The X and Y rails each lie on a plane parallel to the other and are operatively connected to each other to permit relative travel of the X and Y rails along the length of the other. The support translation member also includes at least one motor for effecting such travel.

The support platform is preferably slidably mounted for travel along the length of the X rail and the X rail is slidably mounted for travel along the length of the Y rail. Alternatively, the support platform is slidably mounted for travel along the length of the Y rail and the Y rail is slidably mounted for travel along the length of the X rail.

The cutter member preferably includes a cutter tip having a proximal engagement end and a distal cutting and retrieval end. The cutter tip defines a passage therethrough. A plunger having a proximal engagement portion is preferably provided for slidable movement through the passage of the cutter tip.

The cutter translation assembly preferably includes a motor and a shaft operatively connected to the motor for movement along the Z axis. The shaft has an engagement sleeve for releasable engagement of the engagement end of the cutting tip. A coupling member is received within the sleeve for releasable engagement with the engagement portion of the plunger.

In an alternative embodiment, the cutter tip does not include the plunger and the plunger forms part of the cutter translation assembly.

In the preferred embodiment, the distal cutting end of the cutter tip is configured for cutting into a section of gelatinous material for retrieving and holding the section of material. There are preferably a plurality of disposable cutter tips with associated disposable plungers. Alternatively, the cutter tips and associated plungers may be reusable following appropriate cleaning or sterilization.

The support platform is configured to hold at least one gelatinous sample container, at least one array of cutter members and at least one transfer container. The configuration may take the form of clasps to hold the various elements in place, precisely configured depressions or raised boundaries for receiving the various elements.

An imager is provided for providing images of samples positioned on the support platform in the sample containers. A display unit is preferably provided for receiving and displaying images of the samples from the imager. The controller, which is preferably a computer in communication with the support translation member and the cutter translation assembly, may have an input device for selecting sample sections represented by the sample images displayed on the display unit that are to be retrieved and a memory and execution tool for determining the X, Y coordinates of the selected sample section on the support platform, determining the distance between the sample X, Y coordinates and moving the X, Y coordinates of the point of intersection between the Z axis and the support platform, and moving the support platform that distance such that the selected sample is aligned with the Z axis and moving the cutter member along the Z axis into position for cutting and retrieving the selected section of the sample.

The present invention also provides a method for retrieving one or more selected samples from a gel. The method may include positioning at least one gel containing samples of interest, a plurality of cutter tips and at least one receiving container on a support platform; taking an image of the gel and displaying the image; and selecting a sample from the displayed image of the gel for retrieval. Thereafter, the support platform is moved to first coordinates along an X axis and a Y axis to place the one of the plurality of cutter tips into alignment with a cutter member. The cutter member is moved into contact with the cutter tip to attach it to the cutter member. The cutter member and the now attached cutter tip are moved out of contact with the plurality of cutter tips. The method continues by moving the support platform to second coordinates along the X and Y axes to place the selected sample into alignment with the cutter member, moving the cutter member along a Z axis into contact with the selected sample, piercing the portion of the gel containing the selected sample with the cutter tip, and withdrawing the cutter member to retrieve the selected sample. Then, the support platform is moved to third coordinates along the X and Y axes to place a receiving container in alignment with the cutter member. The selected sample is released to the receiving container. Where retrieval of additional samples is desired, the method further includes releasing the cutter tip following release of the selected sample and repeating the foregoing steps for each of a desired number of different samples using a different one of the plurality of cutter tips for each sample retrieval.

The invention is particularly useful in the field of molecular biology for rapidly collecting numerous specified fractions of samples of biomolecules, such as nucleic acid fragments, DNA, RNA or protein, that are separated by gel electrophoresis; or microorganisms, such as bacteria or yeast that is grown on agarose plates. The apparatus of the present invention is capable of multiple sample retrieval from such gels without cross-contamination from previously excised samples.

DETAILED DESCRIPTION OF THE INVENTION

Figure 1:
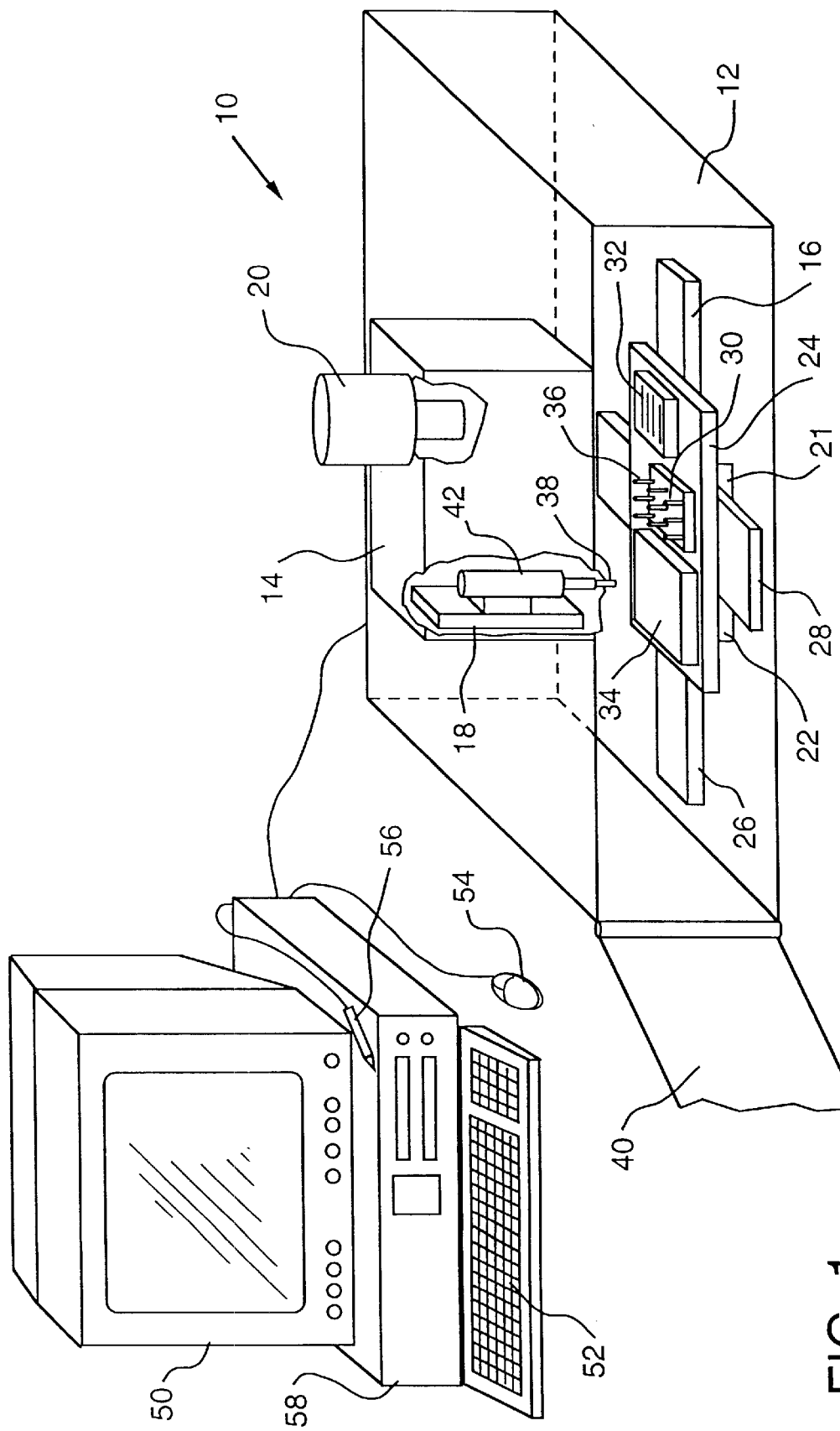
FIG. 1 is a perspective cut away view of the sample retrieval apparatus of the present invention.

An embodiment of the sample retrieval apparatus 10 is shown in FIG. 1. The apparatus shown includes two light-tight housing structures 12 and 14 which house, respectively, a support platform 24 and a support translation member 16 in the base housing 12 and a gel imaging system 20 and a cutter assembly 18 in the upper housing 14.

The housing structures 12, 14 may be constructed of any suitable material for light-tight imaging, such as a metal, black acrylic, or other plastics. While shown in upper and base housing structures, those skilled in the art will recognize that any housing will suffice. The housing structures may be modular or may form a unitary structure. A single housing, not separated into apparent sections may also be used.

With reference again to FIG. 1, the base housing structure 12 has an access door 40 for inserting and removing the support platform 24 and its contents. The support platform 24 may be constructed of any suitable material. In a preferred embodiment, the support platform 24 is constructed of black acrylic. The support platform 24 is preferably configured to hold one or more containers 34 of sample containing gelatinous materials, at least one cutting tip rack 30, and at least one receiving container 32. In a preferred embodiment, the support platform 24 is compartmentalized so as to have either preformed depressions or raised walls outlining where the gel 34, cutting tip rack 36 and receiving container 32 are positioned. Any suitable receiving container will suffice, such as a multi-well processing plate, a rack of one or more test tubes (not shown), or another gel container, depending on the nature of the sample and the desired further use thereof following retrieval. In use, the gel 34, the cutting tip rack 30 and receiving container 32 are positioned on the support platform 24. The gel 34, rack 30 and container 32 are preferably removable and are positioned on the support platform 24 when the apparatus 10 is being prepared for use. In an alternative embodiment, the rack 30 may be fixed to the support platform 24.

The support platform 24 is able to move in two dimensions along an X axis and a Y axis through its connection to the support translation member 16. The translation member 16 includes an X axis rail 26 and a Y axis rail 28. In a preferred embodiment, the Y axis rail 28 rests on top of, and is slidably attached to, the X axis rail 26 while the support platform 24 rests on top of, and is slidably attached to, the Y axis rail 28. The Y axis rail 28 moves along the X axis rail 26 in the direction of the X axis to designated X axis coordinates. The support platform 24 moves along the Y axis rail 28 in the direction of the Y axis to designated Y axis coordinates. Alternatively, the positions of the X and Y axis rails 26, 28 may be reversed. The movement is effected by motors 21 and 22 which are in communication with and controlled by a control device, such as computer 58. Each motor is able to move the support translation member 16 in one of the X axis or Y axis directions. Alternatively, a single motor capable of moving the support translation member 16 in both the X axis and Y axis directions may be used. In one embodiment, the support translation member 16 is connected via the motor 22 to a port in a workstation or other compatible system, such as a Silicon Graphic Inc. workstation, by means of serial communication, for example through an RS232 connector. In use, as the support platform 24 moves in either the X axis and/or Y axis directions, gel 34, cutting tip rack 30 and receiving container 32 all move together as a unit.

The upper housing structure 14 contains a cutter assembly 18 and a gel imaging system 20. The gel imaging system 20 includes a camera, filters and light source. The system 20 images the gel 34 so the user can determine which spots, bands or plaques should be excised. The gel imaging system 20 can use many different kinds of light and in multiple wavelengths, including ultraviolet, visible and far red, depending on the stain used in the gel. By imaging the gel 34 in multiple wavelengths, the gel's image may be projected to a display device 50, such as a computer monitor.

In a preferred embodiment, the gel imaging system 20 includes a CCD camera and filter wheel. Two fiber optic cables connected to two 100W quartz-tungsten-halogen lamps are fitted with the motorized filter wheels. In addition, a video camera may be connected to a fiber optic scope aimed at the cutter assembly 18, and in particular, at the cutter member 38 to allow the user to monitor the process without opening the housing and exposing the interior to outside light. In the preferred embodiment, the CCD camera is connected to a computer 58 via the SCSI port. The filter wheel controllers are connected to computer 58 via a parallel port. Those familiar with computer design and architecture will understand that other means of communication between the elements of the imaging system and the computer or other control or display device may be substituted.

Figure 2:
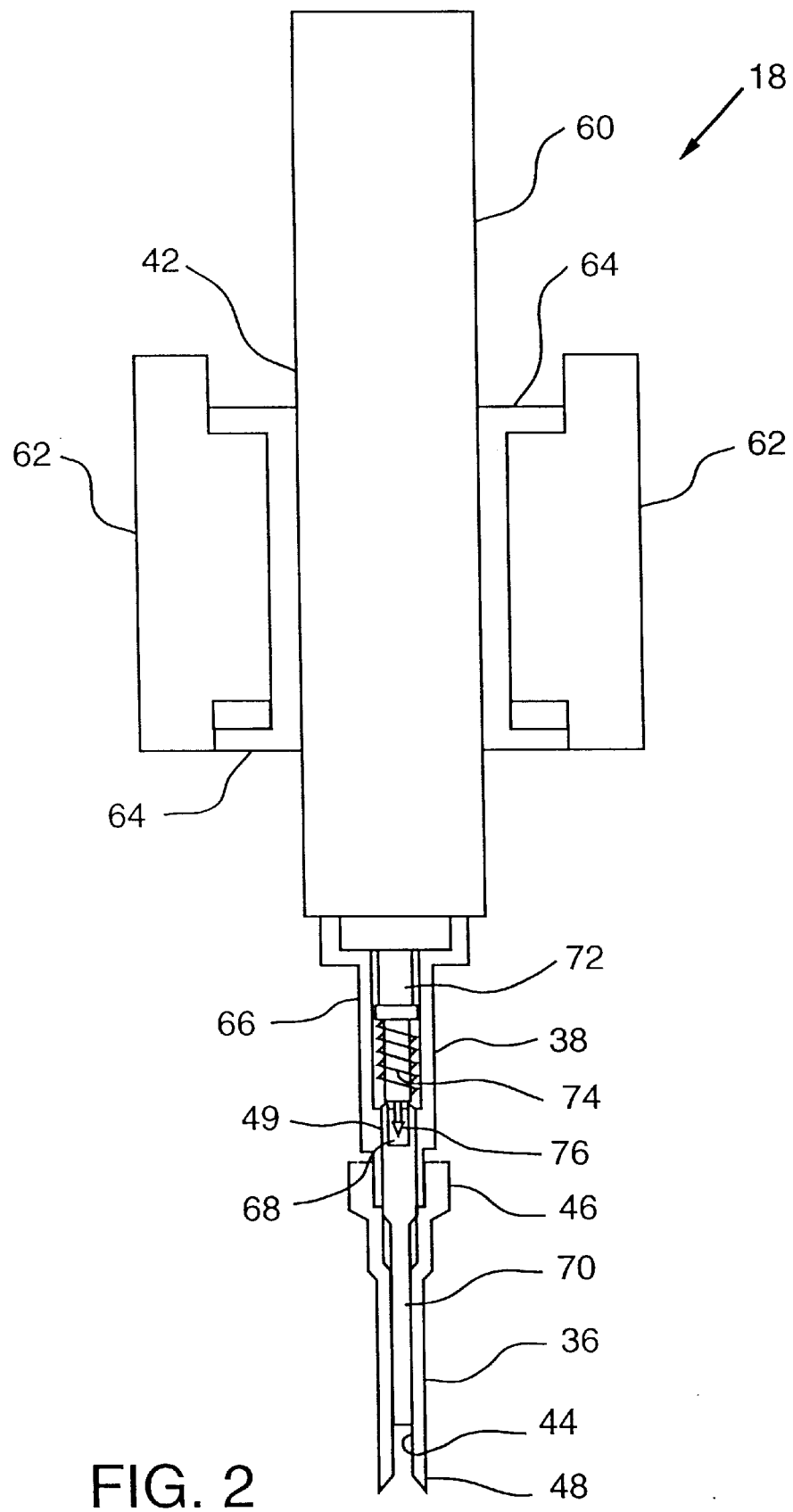
FIG. 2 is a side view of the gel cutting assembly used in the sample retrieval apparatus of FIG. 1.

The upper housing structure 14 also contains the cutter assembly 18, as shown in FIG. 2. The cutter assembly 18 includes a cutter member 38 and a cutter translation assembly 42. The cutter member 38 includes cutting tips 36 and, in the preferred embodiment, an associated plunger 70. The cutting tip 36 has a proximal engagement end 46 and a distal cutting and retrieval end 48 and defines a passage 44 therethrough. The plunger 70 is slidably mounted in the passage 44 and has a proximal engagement portion 49.

The cutter translation assembly 42 is mounted to the upper housing structure 14 in such a manner that it is capable of moving in a third dimension, along a Z axis. The cutter translation assembly 42 includes a motor mount 62 fixedly attached to the upper housing structure 14, a motor mount sleeve 64 attached to the motor mount 62, and a linear stepping motor 60 which is fixedly attached to the motor mount sleeve 64. The motor mount sleeve 64 is moveably attached to the motor mount 62 such that the sleeve 64 passively travels or slips a desired distance along the Z axis.

In the preferred embodiment, the distance of travel or slippage of the sleeve 64 in the mount 62 is approximately ¼ inches. Greater or lesser distances may be used to accommodate the dimensions of the overall apparatus design. Attached to the bottom surface of the linear stepping motor 60 is a hollow tip holding sleeve 66. The linear stepping motor 60 and its attached tip holding sleeve 66 move along the Z axis, which movement is controlled, in one embodiment, by means of an operative connected to a computer 58 via a serial connection, such as an RS232 connector. Other suitable known means of control will suffice.

Inside the hollow tip holding sleeve 66, the linear stepping motor 60 drives a drive shaft 72 which pushes a spring-loaded coupling shaft 74 in the Z' axis direction. The drive shaft 72 and the spring-loaded coupling shaft 74 can be one or two pieces, so they may or may not be threaded together. The tip holding sleeve 66 engages the proximal engaging end 46 of cutting tips 36, which fit snugly onto the end of the tip holding sleeve 66. The coupling shaft 74 has a knurled end 76 which is inserted into a slot 68 in the proximal end 49 of a plunger 70.

The spring-loaded coupling shaft 74 acts as a piston to move the plunger 70 in the Z' axis direction. The plunger 70 may be fixedly attached to coupling shaft 74 or form a contiguous structure with shaft 74 provided the plunger 70 does not contact the samples in use. However, in the preferred embodiment, the plunger 70 and a cutting tip 36 form the cutter member 38. The plunger 70 and the cutting tip 36 are preferably disposable, but may be reusable after cleaning. The plunger 70 is proportioned to fit and slide freely within an axial passage 44 through the cutting tip 36 while still maintaining a fit that is tight enough to create suction. The spring-loaded coupling shaft 74 moves the plunger 70 upwards and downwards, such that the plunger 70 travels freely inside the cutting tip 36. In one embodiment, the motor controller for the coupling shaft 74 is operatively connected to a computer 58 through a second port via a serial connection, such as an RS232 connector. Any suitable known device for controlling the movement of the coupling shaft 74 and plunger 70 will suffice.

The apparatus 10 is also comprised of a display device 50, an input device 52, 54, 56 and a control device 58 as shown in FIG. 1. The display device 50 is used for displaying an image of the sample, such as spot, band or plaque patterns on the gel 34. The input devices 52, 54 or 56 allow the user to choose specific spots, bands or plaques of interest for excision. For example, the computer mouse 54 may be used to highlight and click on the selected sample. Alternatively, an electronic pen 56 may be used to circle the selected sample. The computer keyboard 52 may be used to key in coordinates matching the location of the selected sample on a grid overlay or cursor keys may be used to identify the selected sample. In yet another embodiment, the selection of the sample from the image may be automatic by means of software programmed to recognize and select specified spots, bands or plaques on a gel.

The control device 58, controls both the support platform 24 and the cutter translation assembly 42 so as to cause the cutter translation assembly 42 to move into the correct position to excise the desired spots, bands or plaques from the gel 34. The input device, such as a computer mouse 54, allows the user to select a desired spot, band or plaque by "clicking" on the spot's, band's or plaque's image while displayed on the display device 50. The control device 58, a computer workstation or other suitable system, employs software to interpret the input data received from the input device and controls both the support platform 24 and the cutter member 38 so as to cause the cutter member 38 to excise the selected spots, bands or plaques from the gel 34.

The control device 58 is programmed to "know" where the gel 34, cutting tip rack 30 and container 32 are located. Because the support platform 24 has specific locations for placement of the gel 34, rack 30 and receiving container 32, the relative distance between locations on those items and a starting point can be determined. The program recognizes starting, or home, X, Y coordinates. The program "knows" where the individual cutting tips 36 in the rack 30 and the individual wells in the container 32 are located by use of delta values to represent the distance between the starting X, Y coordinates and the X, Y coordinates of the consecutive cutting tips 36 and positions in the receiving container area. For example, the positions of the center of each well in a standard sized container are preprogrammed. Similarly, the distance between cutter tips in the rack, the location of differently sized tips and the rows of tips or other alignment of tips in the rack can be determined and preprogrammed. The delta values used to determine the X, Y coordinates of the selected gel sample may be, for example, based on pixels in the image of the gel. When a selection of a portion of the image representative of a sample on the gel is made, the distance in pixels in the image translates into discrete distance units on the actual gel and is converted into corresponding X, Y coordinates to pin the location of the sample on the support platform. The computer 58 then directs the movement of the platform 24 to the designated X, Y coordinates. The relative heights of the items on the platform 24 along the Z axis and the Z' axis and the delta values between a withdrawn position and an engaged position are also preprogrammed.

The sample retrieval apparatus 10 operates as follows. First, the user places the gel 34, cutting tip rack 30 and receiving container, for example, the multi-well processing plate 32, on the support platform 24. The gel 34 will usually be a polyacrylamide electrophoresis gel but can also be an agar plate used to grow microorganisms or any other kind of gel or material of similar consistency. Next, the user images the gel 34 in multiple wavelengths using the gel imaging system 20. To determine the proper exposure conditions, the support platform 24 is moved to predefined X, Y coordinates to position the gel 34 under the camera. When the conditions suitable for creating acceptable images are determined, the camera and filter are set to the appropriate settings. Because the CCD field-of-view is much smaller than the area of the gel, a composite set of tiled images is recorded so that the entire gel is imaged. In the tiling routine, the CCD camera scans back and forth across the gel 34 starting from one corner and moving systematically across and down the entire gel to the diagonal corner until images of the entire gel have been taken and stored. The tiled images are computationally assembled to create one complete image of the gel 34. One composite image is created for each dye-labeled sample on the gel 34. The gel's image is displayed on the display device 50 and the user can select a portion of the sample, such as the spots, bands or plaques of interest, based on visual inspection using one of the input devices 52, 54 or 56. The selection can also be based on the results of commercially available automated protein difference detection software.

As shown in FIGS. 1 and 2, in order to engage a cutting tip 36, the control device 58 directs the movement of the support platform 24 from its home position to a first X, Y coordinate position such that the tip holding sleeve 66 is aligned above the first available cutting tip 36 in the rack 30. The tip holding sleeve 66 is then lowered and the linear stepping motor 60 drives the drive shaft 72 which then moves the spring-loaded coupling shaft 74 downward to engage the plunger 70. The assembly is then raised to remove the cutting tip 36 from the rack 30. The spring-loaded coupling shaft 74 then moves the plunger 70 down the passage 44 of the cutting tip 36 to give a 1 to 2 mm gap between the end of the plunger 70 and the tip of the cutting tip 36.

Figure 3:
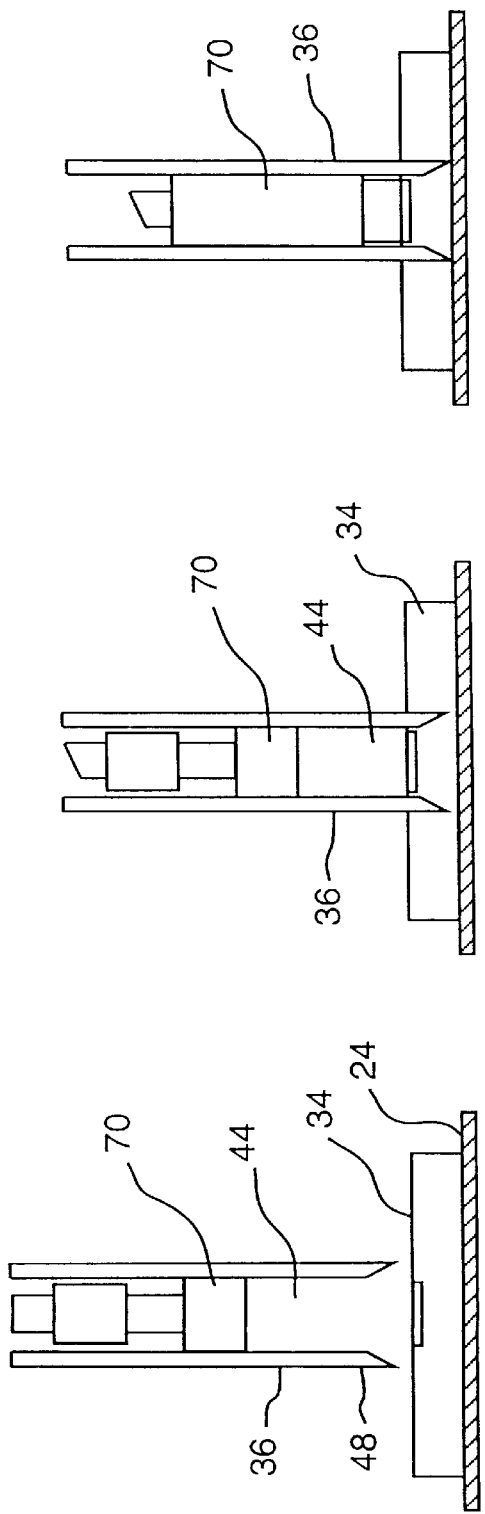
FIGS. 3 (a)–(e) illustrates the sequence of operations involved in excising a selected sample from a gel.

Next, the control device 58 directs the movement of the support platform 24 to another X, Y coordinate to position the selected spot, band or plaque of the sample in alignment with the cutter member 38. At this time, the user may wish to inspect the position of the cutting tip 36 relative to the selected sample by using the video camera. If the alignment was not correct, adjustments can be made by means of a manual adjustment of the support platform 24 or, preferably, by adjusting the origin parameters through the computer program control. If positioned correctly, the cutter member 38 with tip 36 attached is then lowered along the Z axis until the disposable cutting tip 36 rests on the gel 34. The cutter member 38 operates as shown in FIG. 3 to use one tip 36 to make one cut in a gel 34 per sample. The weight of the cutter member 38 causes the motor mount sleeve 64 to slip against the motor mount 62 so that the cutting tip 36 slices into the gel 34. The cutting tip 36 has a negative bevel to allow for easier excision of spots, bands or plaques from the gel 34. After the tip 36 slices into the gel 34, the plunger 70 is withdrawn along the Z' axis enough to create a suction to hold the excised gel section within the passage 44. The cutter member 38 is then raised to remove the selected spot, band or plaque from the gel 34.

The control device 58 then directs the movement of the support platform 24 to third X and Y coordinates to position the cutter member 38 above the first available well in the multi-well processing plate 32 or other receiving container for transfer of the selected sample. The wells in the multi-well processing plate 32 are preferably pre-filled with solution required for processing of the sample. The cutter member 38 is then lowered along the Z axis to position the cutting tip 36 over the surface of the processing solution and the spring-loaded coupling shaft 74 extends the plunger 70 along the Z' axis within the passage of the cutting tip 36 to eject the selected sample in the gel fragment into the processing solution. Following ejection of the sample, the cutter member 38 is raised.

Next, the control device 58 directs the movement of the support platform 24 to the first X, Y coordinates to position the cutting tip 36 above the location in the rack 30 from which it was originally taken. The cutter member 38 is then lowered and deposits the tip 36 back into the rack 30 before being raised to its initial position. The control device 58 then directs the movement of the support platform 24 to its original starting position. The foregoing sample retrieval procedure is repeated as many times as desired. As a result, the sample retrieval apparatus 10 is able to retrieve multiple samples from molecular biology gels without cross-contamination from previously excised samples.

Figure 4:
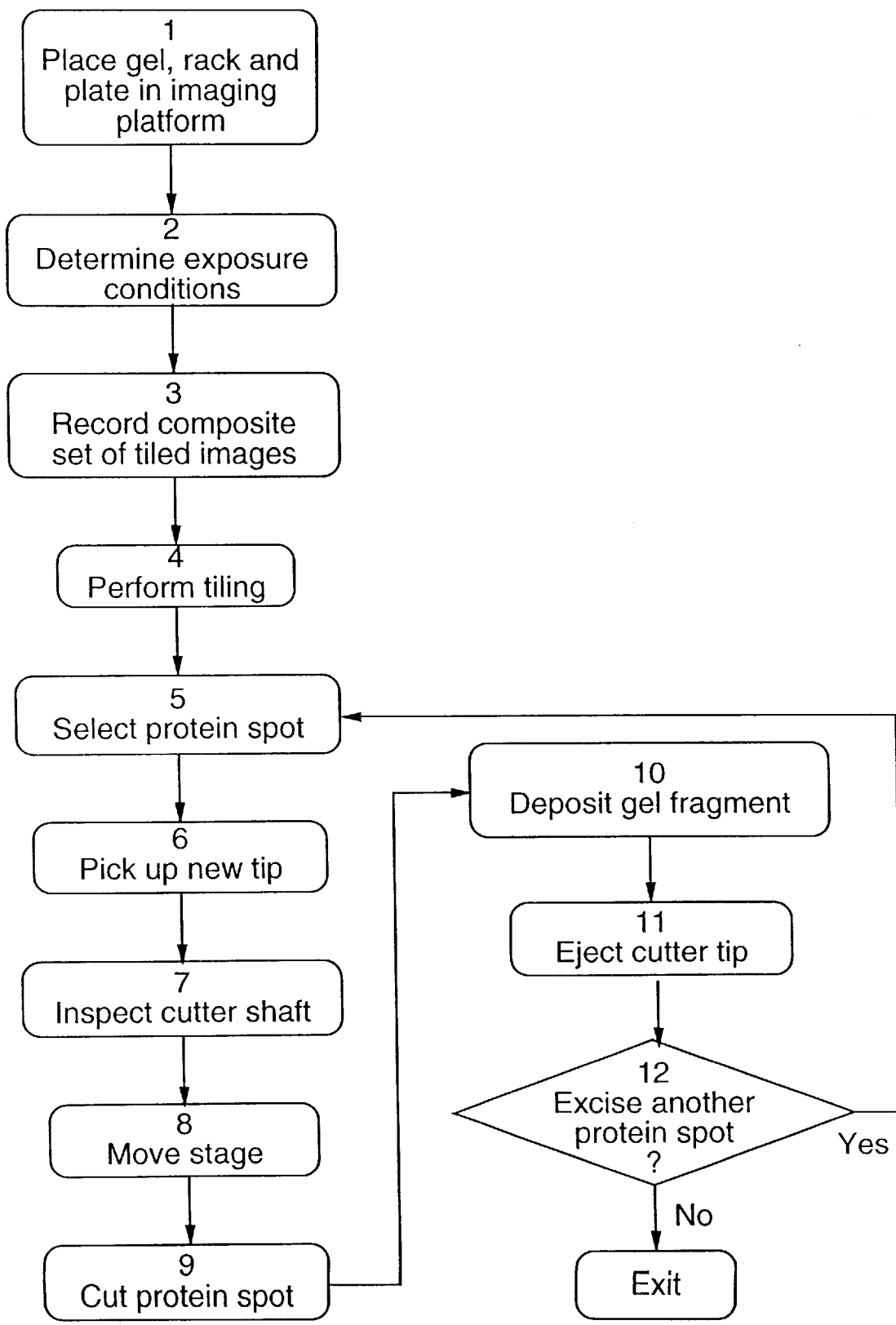
FIG. 4 is a schematic of the gel imaging and cutting routine where one cutting tip is used to make one cut per sample.
Figure 6:
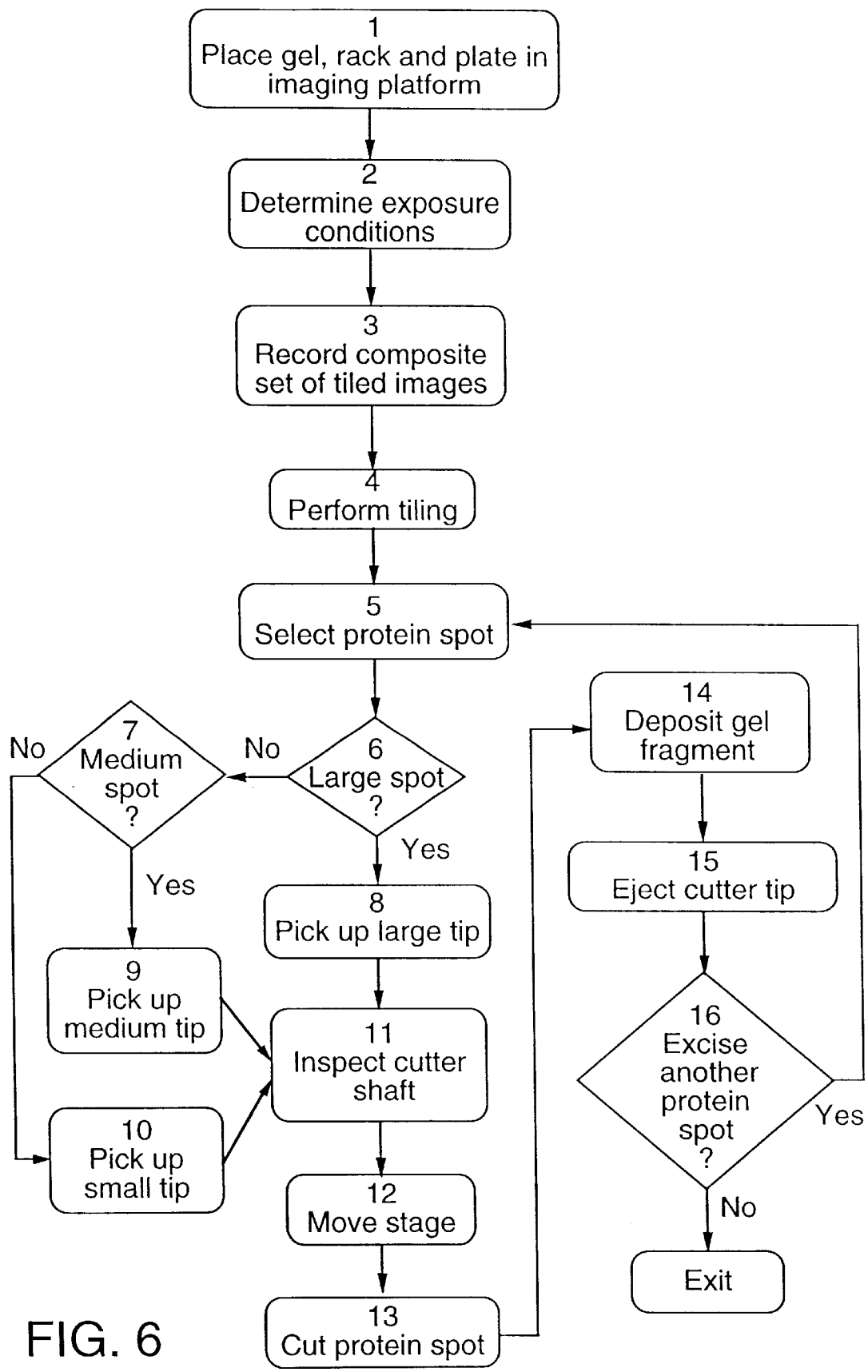
FIG. 6 is a schematic of the gel imaging and cutting routine where different sized cutting tips are used to make one cut per sample.

Another embodiment of the invention allows for single cuts to be made in a gel 34 using a plurality of different size cutting tips 36 in order to excise different size spots, bands or plaques in the gel 34. A schematic of the gel imaging and cutting routine used in this embodiment is shown in FIG. 6. The different size cutting tips 36 are all designed with the same size proximal engaging ends 46 to fit on the same tip holding sleeve 66. The difference between this embodiment and the general embodiment shown in FIG. 4 is that this embodiment has the additional step of allowing the user to select the size of the cutting tip 36 using the input device 52, 54 or 56. Preferably, however, the size of the cutting tip 36 will be automatically calculated by the computer 58 based on the size of the sample selected. There may be several pre-set sizes for circles surrounding a selected sample defining for example, small, medium and large or extra large protein spots. Each circle size corresponds to a different size cutting tip 36. The tip rack 30 is filled with the different sized tips 36 in predefined positions within rack 30.

Figure 5:
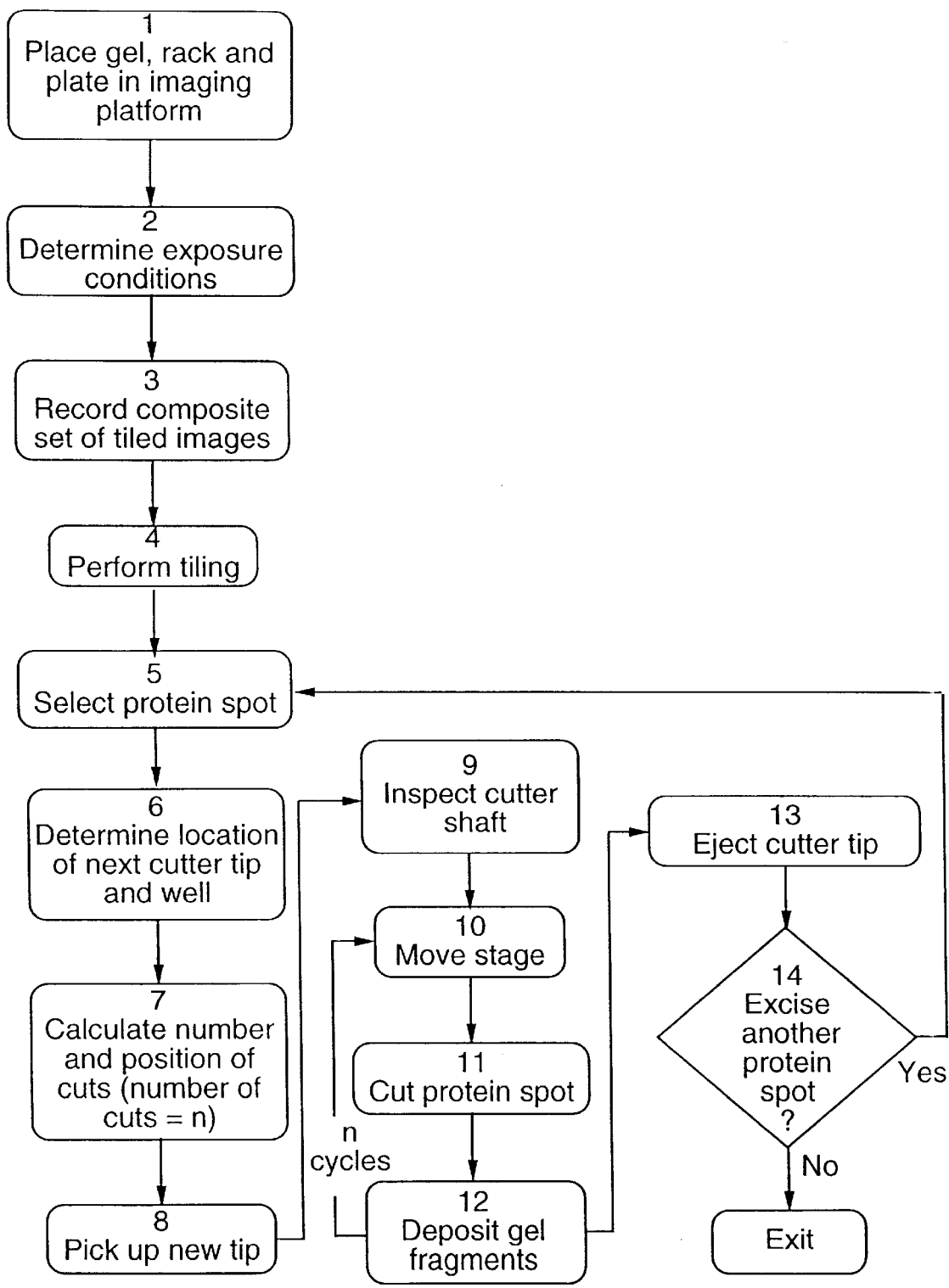
FIG. 5 is a schematic of the gel imaging and cutting routine where one cutting tip is used to make multiple cuts per sample.

A further embodiment of the invention allows for a single cutting tip 36 to make several cuts in a large band or plaque in order to excise the entire band or plaque before exchanging tips and subsequently excising a new band or plaque. A schematic of the gel imaging and cutting routine used in this embodiment is shown in FIG. 5. The difference between this embodiment and the general embodiment shown in FIG. 4 is that this embodiment has the additional step of calculating the number of cuts (n) needed to excise the entire spot, band or plaque and then repeating the cutting process n times before ejecting the cutter tip 36.

Although the foregoing invention has been described in detail using illustrations and specific commercial components for clarity, it will be apparent to persons having ordinary skill in the art in light of the detailed description and drawings, that certain changes and modifications may be made thereto without departing from the spirit and scope of the invention.

What is claimed is:

1. A sample retrieval apparatus comprising:
   a support platform;
   a support translation member for moving the support platform to designated coordinates on X and Y axes;
   a plurality of cutter members on the support platform;
   a cutter translation assembly for moving a selected one of the cutter members to designated positions on a Z axis, said Z axis lying in a plane perpendicular to the support platform; and,
   a controller for designating the X, Y axis coordinates of the support platform and the Z axis positions of the cutter members.

2. The apparatus recited in claim 1 wherein the support translation member is comprised of an elongate X rail lying on the X axis and an elongate Y rail lying on the Y axis, the X and Y rails each lying on a plane parallel to the other and being operatively connected to each other to permit relative travel of the X and Y rails along the length of the other; and, at least one motor for effecting such travel.

3. The apparatus recited in claim 2 wherein the support platform is slidably mounted for travel along the length of the X rail and the X rail is slidably mounted for travel along the length of the Y rail.

4. The apparatus recited in claim 2 wherein the support platform is slidably mounted for travel along the length of the Y rail and the Y rail is slidably mounted for travel along the length of the X rail.

5. The apparatus recited in claim 1 wherein:

each cutter member of the plurality of cutter members is comprised of:

a cutting tip having a proximal engagement end and a distal cutting and retrieval end and defining a passage therethrough; and, a plunger slidably mounted in the passage, the plunger having a proximal engagement portion; and, the cutter translation assembly is comprised of:

a motor;

a shaft operatively connected to the motor for movement along the Z axis, the shaft having an engagement sleeve for releasable engagement of the engagement end of the cutting tip; and, a coupling member received within the sleeve for releasable engagement with the engagement portion of the plunger.

6. The apparatus recited in claim 1 wherein each cutter member of the plurality of cutter members is comprised of a cutter tip having a proximal engagement end and a distal cutting and retrieval end and defining a passage therethrough.

7. The apparatus recited in claim 6 wherein the cutter translation assembly is comprised of a motor;

a shaft operatively connected to the motor for movement along the Z axis, the shaft having an engagement sleeve for releasable engagement of the engagement end of the selected one of the cutting tips; and, a plunger having a proximal end received within the engagement sleeve and a distal end sized for insertion into the passage of the selected one of the cutting tips.

8. The apparatus recited in claim 6 wherein the distal cutting end is configured for cutting into a section of gelatinous material for retrieving and holding the section of material.

9. The apparatus recited in claim 1 further comprising:

an imager for providing images of samples positioned on the support platform.

10. The apparatus recited in claim 1 further comprising:

an imager for providing images of samples positioned on the support platform;

a display unit for receiving and displaying images of the samples from the imager;

wherein the controller has an input device for selecting sample sections represented by the sample images displayed on the display unit that are to be retrieved and a memory and execution tool for determining the X, Y coordinates of the selected sample section on the support platform, determining the distance between the sample X, Y coordinates and the X, Y coordinates of a point of intersection between the Z axis and the support platform, and moving the support platform said distance such that the selected sample is aligned with the Z axis and moving a selected one of the cutter members along the Z axis into position for cutting and retrieving the selected section of the sample.

11. The apparatus recited in claim 10 wherein the controller is a computer in communication with the support translation member and the cutter translation assembly.

12. A sample retrieval apparatus comprising:

a support platform;

a support translation member for moving the support platform to designated coordinates on X and Y axes;

a plurality of disposable cutter members on the support platform, each cutter member being comprised of a cutting tip having a proximal engagement end and a distal cutting and retrieval end and defining a passage therethrough, and a plunger slidably mounted in the passage, the plunger having a proximal engagement portion;

a cutter translation assembly for moving a selected one of said cutter members to designated positions on a Z axis, said Z axis lying in a plane perpendicular to the support platform, the cutter translation assembly being comprised of a motor, a shaft operatively connected to the motor for movement along the Z axis, the shaft having an engagement sleeve for releasable engagement of the engagement end of the cutting tip, and a coupling member received within the sleeve for releasable engagement with the engagement portion of the plunger; and, a controller for designating the X, Y axis coordinates of the support platform and the Z axis positions of the selected cutter member.

13. A sample retrieval apparatus comprising:

a support platform;

a support translation member for moving the support platform to designated coordinates on X and Y axes;

a plurality of disposable cutter tips on the support platform, each cutter tip having a proximal engagement end and a distal cutting and retrieval end and defining a passage therethrough;

a cutter translation assembly for moving a selected one of the cutter tips to designated positions on a Z axis, said Z axis lying in a plane perpendicular to the support platform; and, a controller for designating the X, Y axis coordinates of the support platform and the Z axis positions of the cutter tips.

14. A sample retrieval apparatus comprising:

a support platform;

a support translation member for moving the support platform to designated coordinates on X and Y axes;

at least one array of cutter members on the support platform;

a cutter translation assembly for moving the cutter member to designated positions on a Z axis, said Z axis lying in a plane perpendicular to the support platform; and, a controller for designating the X, Y axis coordinates of the support platform and the Z axis positions of the cutter member, wherein the support platform is configured to hold at least one gelatinous sample container, said at least one array of cutter members and at least one receiving container.

15. The apparatus recited in claim 14 wherein the gelatinous sample container is an electrophoresis gel plate containing bands of biomolecules.

16. The apparatus recited in claim 14 wherein the gelatinous sample container is an agarose dish containing plaques of microorganisms.

17. The apparatus recited in claim 14 wherein the receiving container is comprised of a plurality of sample receiving sections.

18. The apparatus recited in claim 14 wherein the array of cutter members comprises a plurality of disposable cutting tips, each tip having an associated plunger.

19. The apparatus recited in claim 18 wherein the plurality of cutter tips includes a plurality of differently sized cutting tips for cutting differently sized samples from the gelatinous sample container.

20. A sample retrieving apparatus comprising:
   a support platform supporting at least one sample containing gel, a supply of cutting tips, and a receiving container thereon;
   a support translation member for moving the support platform two dimensionally along an X axis and a Y axis;
   a gel cutter assembly capable of moving in a third dimension, along a Z axis;
   a gel illumination system;
   a display device for displaying thereon an image of the gel;
   an input device for choosing a desired portion of the gel; and
   a control device for controlling the translation member and the gel cutter assembly so as to cause the gel cutter assembly to excise the desired portion and deposit the excised portion into the receiving container.

21. The gel cutting assembly recited in claim 20 comprising:
   a linear stepping motor;
   a motor mount sleeve moveably connected to the linear stepping motor;
   a motor drive shaft extending from the linear stepping motor;
   a tip holding sleeve connected to the linear stepping motor and around the motor drive shaft;
   a cutting tip defining a passage therethrough and being releasably connected to the tip holding sleeve;
   a plunger positioned for sliding within the passage of the disposable cutting tip,
   a spring-loaded coupling shaft connected to the motor drive shaft on one end thereof and to the disposable plunger on the other end thereof for effecting linear movement of the plunger within the passage of the cutting tip.

22. The apparatus recited in claim 21 wherein the plunger is releasably attached to the coupling shaft.

23. The apparatus recited in claim 22 wherein the plunger and the cutting tip are disposable.

24. A method for retrieving a sample from a gel comprising:
   (a) positioning at least one gel containing samples of interest, a plurality of cutting tips and at least one receiving container on a support platform;
   (b) taking an image of the gel and displaying the image;
   (c) selecting a sample from the displayed image of the gel for retrieval;
   (d) moving the support platform to first coordinates along an X axis and a Y axis to place one of the plurality of cutter tips into alignment with an operative portion of a cutter translation assembly;
   (e) moving the operative portion into contact with the plurality of cutting tips to attach one of the cutting tip to the operative portion;
   (f) moving the operative portion and the cutter tip out of contact with the plurality of cutter tips;
   (g) moving the support platform to second coordinates along the X and Y axes to place the selected sample into alignment with the cutting tip;
   (h) moving the cutting tip into contact with the selected sample;
   (i) piercing the sample with the cutting tip;
   (j) withdrawing the cutting tip to retrieve the selected sample; and
   (k) moving the support platform to third coordinates along the X and Y axes to place a receiving container in alignment with the cutting tip and the retrieved selected sample; and,
   (l) releasing the selected sample to the container.

25. The method of claim 24 further comprising releasing the cutting tip following release of the selected sample and repeating steps (b) through (k) for each of a desired number of different samples using a different one of the plurality of cutting tips.

26. A method for retrieving at least one sample from a gel comprising:
   (a) positioning at least one gel containing samples of interest and a plurality of cutting tips on a support platform;
   (b) selecting a sample from the gel for retrieval;
   (c) moving the support platform to first coordinates along an X axis and a Y axis to place one of the plurality of cutter tips into alignment with an operative portion of a cutter translation assembly;
   (d) moving the operative portion into engagement with one of the plurality of cutting tips;
   (e) moving the support platform to second coordinates along the X and Y axes to place the selected sample into alignment with the engaged cutting tip;
   (f) moving the engaged cutting tip into contact with the selected sample;
   (g) retrieving the sample with the engaged cutting tip;
   (h) moving the support platform to third coordinates along the X and Y axes to release the selected sample to a container;
   (i) releasing the engaged cutting tip; and,
   (j) optionally repeating steps (b) through (i) until a desired number of samples have been retrieved.

* * * * *